(12) United States Patent
McKnight et al.

(10) Patent No.: US 8,815,780 B2
(45) Date of Patent: Aug. 26, 2014

(54) PLATFORM FOR IMMOBILIZATION AND OBSERVATION OF SUBCELLULAR PROCESSES

(75) Inventors: Timothy E. McKnight, Greenback, TN (US); Udaya C. Kalluri, Knoxville, TN (US); Anatoli V. Melechko, Raleigh, NC (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 13/369,849

(22) Filed: Feb. 9, 2012

(65) Prior Publication Data
US 2013/0210649 A1    Aug. 15, 2013

(51) Int. Cl.
| | | |
|---|---|---|
| *C40B 30/06* | (2006.01) | |
| *C12N 11/04* | (2006.01) | |
| *A01N 1/00* | (2006.01) | |
| *C12M 3/00* | (2006.01) | |

(52) U.S. Cl.
CPC ................................. *C40B 30/06* (2013.01)
USPC ........ 506/10; 435/182; 435/284.1; 435/287.1

(58) Field of Classification Search
CPC ..................................................... C40B 30/04
USPC ............................................ 506/10; 435/177
See application file for complete search history.

(56) References Cited

U.S. PATENT DOCUMENTS

| | | | |
|---|---|---|---|
| 6,649,431 B2 | 11/2003 | Merkulov et al. | |
| 6,692,324 B2 | 2/2004 | Simpson et al. | |
| 6,958,572 B2 | 10/2005 | Merkulov et al. | |
| 6,982,519 B2 | 1/2006 | Guillorn et al. | |
| 7,109,515 B2 | 9/2006 | Merkulov et al. | |
| 7,144,287 B2 | 12/2006 | Guillorn et al. | |
| 7,229,692 B2 | 6/2007 | Melechko et al. | |
| 7,245,068 B2 | 7/2007 | Merkulov et al. | |
| 7,408,186 B2 | 8/2008 | Merkulov et al. | |
| 7,641,863 B2 | 1/2010 | Doktycz et al. | |
| 2002/0117951 A1 | 8/2002 | Merkulov et al. | |
| 2004/0173506 A1 | 9/2004 | Doktycz et al. | |
| 2004/0186459 A1* | 9/2004 | Shur et al. ..................... | 604/500 |
| 2004/0197909 A1* | 10/2004 | McKnight et al. ............ | 435/440 |
| 2005/0017173 A1 | 1/2005 | Kumar | |
| 2014/0030788 A1 | 1/2014 | Chen et al. | |

OTHER PUBLICATIONS

Wu et al., "Culture and chemical-induced fusion of tobacco mesophyll protoplasts in a microfluidic device", Microfluid Nanofluid (2011), vol. 10, pp. 867-876.
Ko et al., "Tobacco protoplast culture in a polydimethylsiloxane-based microfluidic channel", Protoplasma (2006), vol. 227, pp. 237-240.

* cited by examiner

*Primary Examiner* — Christopher M Gross
*Assistant Examiner* — Richard L Manteuffel
(74) *Attorney, Agent, or Firm* — Scully, Scott, Murphy & Presser, P.C.

(57) ABSTRACT

A method of immobilizing matter for imaging that includes providing an array of nanofibers and directing matter to the array of the nanofibers. The matter is immobilized when contacting at least three nanofibers of the array of nanofibers simultaneously. Adjacent nanofibers in the array of nanofibers may be separated by a pitch as great as 100 microns. The immobilized matter on the array of nanofibers may then be imaged. In some examples, the matter may be cell matter, such as protoplasts.

10 Claims, 4 Drawing Sheets

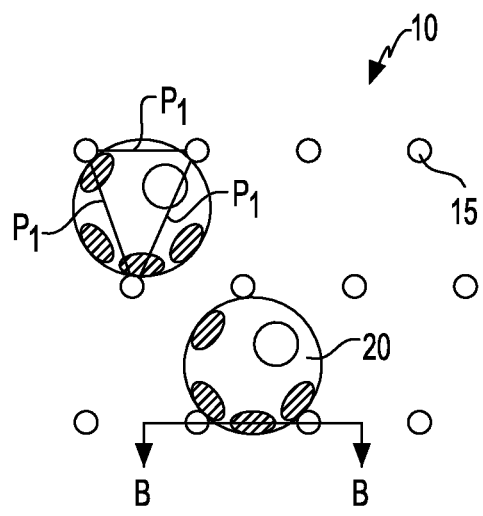
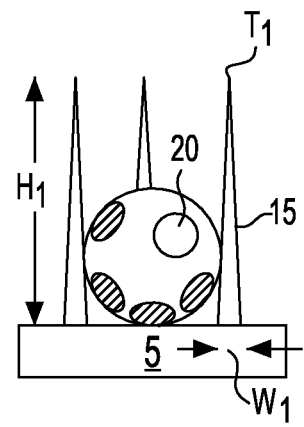
FIG. 1A
FIG. 1B
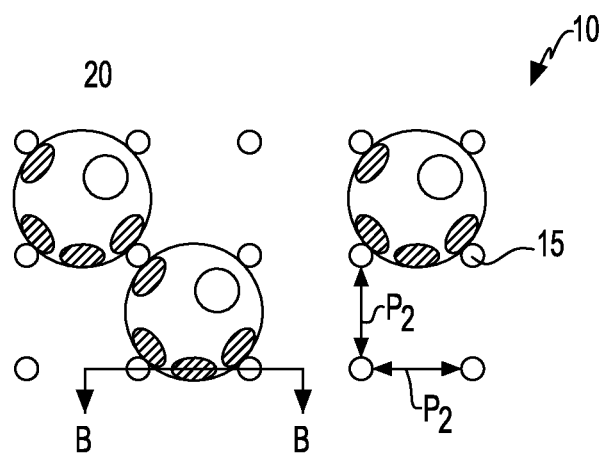
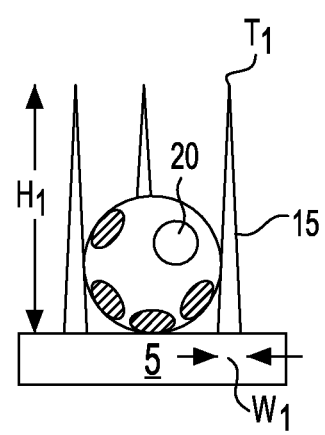
FIG. 2A
FIG. 2B

PLATFORM FOR IMMOBILIZATION AND OBSERVATION OF SUBCELLULAR PROCESSES

This invention was made with Government support under Contract No. DE-AC05-00OR22725 awarded by the United States Department of Energy. The Government has certain rights in this invention.

BACKGROUND

The present disclosure is related to observation of cellular materials, and more particularly to platforms for observing cellular materials.

One requirement for investigating cellular-level processes, such as cell growth, cell wall or cellulose biosynthesis and other dynamic responses, is the ability to monitor large numbers of individual cells, tissue fragments, and/or protoplasts over extended time periods. To achieve maximum resolution, high powered objectives are necessary which can typically only capture small numbers of cells in any single field of view. Therefore, it can be necessary to iteratively image different regions of a culture over the course of the experiment. Translation of the sample stage is typically required to observe several different specimens in different fields of view over the course of the experiment. If the specimens, such as protoplasts, that are being observed are not immobilized, they will typically move around within the culture chamber during these manipulations. Even without macroscale movement of the experiment, protoplasts may shift position just due to natural convection and/or vibrations of the systems.

SUMMARY

In one embodiment, nanostructured, high-aspect-ratio spike arrays are provided for immobilizing matter, such as cell matter, e.g., protoplasts, for temporal evaluation. Spike arrays may be fabricated at defined interspike dimensions to provide three or four point pinning of individual protoplasts. In one embodiment, the method of immobilizing cell matter for imaging includes providing an array of nanofibers, in which adjacent nanofibers in the array of nanofibers are separated by a pitch of less than 100 microns. Cell matter may then be directed to the array of the nanofibers, wherein the cell matter is immobilized when simultaneously in contact with at least three nanofibers of the array of nanofibers. The cell matter that is immobilized in the array of nanofibers may then be imaged.

In another aspect, a structure is provided for immobilizing matter, such as cell matter, multicellular tissues, extracellular matrices, and organic and inorganic solids. In one embodiment, the structure for immobilizing matter includes a channel for delivery of a fluid containing matter, and an array of nanofibers positioned within the channel having a pitch between adjacent nanofibers in the array of nanofibers ranging from 3 microns to 20 microns. Each of the nanofibers in the array of nanofibers has a tip diameter of 150 nm or less, and each of the nanofibers has an increasing diameter from the tip diameter to a base of each of the nanofibers. The combination of the pitch between adjacent nanofibers and the increasing diameter of the nanofibers provides dimensions that physically engage matter from the fluid containing matter that is delivered to the array of nanofibers. The matter is physically engaged when in simultaneous contact with at least three nanofibers of the array of nanofibers.

In another aspect, a method of analyzing matter response to external stimuli is provided that includes providing a platform including a channel and an array of nanofibers within the channel. In one embodiment, the method for analyzing matter includes providing a channel having an array of nanofibers within the channel. A first portion of the array of nanofibers has a pitch between adjacent nanofibers that immobilizes matter. A second portion of the array of nanofibers is separated from walls of the channel and provides at least one electrode. A fluid containing matter is passed through the channel, wherein the fluid containing matter is traversed across the first portion of the array of nanofibers before the second portion of the array of nanofibers. As the fluid containing matter is traversed past the first portion of the array of nanofibers, at least a portion of the matter contained within the fluid containing matter is immobilized by the first portion of the array of nanofibers. A stimuli is then applied to the matter that is immobilized by the first portion of the array of nanofibers. Emissions and secretions by the matter in response to the stimuli may be measured with the at least one electrode that is provided by the second portion of the array of nanofibers. The matter may be cell matter, such as protoplasts.

In another aspect, a structure is provided for immobilizing matter, and measuring emissions by the immobilized matter in response to stimuli that is applied to the immobilized matter. In one embodiment, the structure for analyzing matter response to external stimuli includes a channel for delivery of a fluid containing matter and an array of nanofibers that is present within the channel. The array of nanofibers includes a first portion that is present at an opening of the channel and a second portion that is present at the exit of the channel. The first portion of the array of nanofibers has a pitch between adjacent nanofibers to physically engage matter from the fluid containing matter being traversed through the channel from the opening to the exit. The second portion of the nanofibers provides at least one electrode that is physically separated from the sidewalls of the channel. The matter being immobilized by the structure may be cell matter, e.g., protoplasts.

BRIEF DESCRIPTION OF THE DRAWINGS

The following detailed description, given by way of example and not intended to limit the disclosure solely thereto, will best be appreciated in conjunction with the accompanying drawings, wherein like reference numerals denote like elements and parts, in which:

FIG. 1A is a top down planar view of an array of nanofibers for immobilizing matter, wherein the matter is immobilized when in contact with three adjacent nanofibers, in accordance with one embodiment of the present disclosure.

FIG. 1B is a side cross-sectional view along section line B-B in FIG. 1A.

FIG. 2A is a top down planar view of an array of nanofibers for immobilizing matter, wherein the matter is immobilized when in contact with four adjacent nanofibers, in accordance with one embodiment of the present disclosure.

FIG. 2B is a side cross-sectional view along section line B-B in FIG. 2A.

DETAILED DESCRIPTION

Detailed embodiments of the present disclosure are described herein; however, it is to be understood that the disclosed embodiments are merely illustrative of the compositions, structures and methods of the disclosure that may be embodied in various forms. In addition, each of the examples given in connection with the various embodiments are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the compositions, structures and methods disclosed herein. References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment.

The present disclosure relates to immobilizing matter for observation. Examples of matter that may be immobilized include cell matter and nutrients. As used herein, the term "cell matter" includes cells, a cell, and the components of a cell, such as organelles. For example, the term "cell matter" may include the nucleus, vacuoles, and mitochondria, all of which may be enclosed within the cell membrane and immersed in cytoplasm. Both animal and plant cells can provide cell matter that is suitable for use with the methods and structures disclosed herein. In some embodiments, the cell matter is provided by protoplasts. A "protoplast" is a plant cell in which the cell wall has been removed. For example, a protoplast may be a plant cell in which the cell wall has degraded away. Following degradation of the cell wall, a plasma remains which provides the protoplast. Protoplasts are typically fragile, and are not easily immobilized for observation. In some embodiments, the structures and methods disclosed herein are suitable for immobilizing matter for observation and treatment with reagents. Although the following disclosure describes the immobilization of cell matter, the present disclosure is not limited to only this type of matter. As the present disclosure is also applicable to other types of matter, such as extracellular materials, and organic/inorganic solids.

Figure 3:
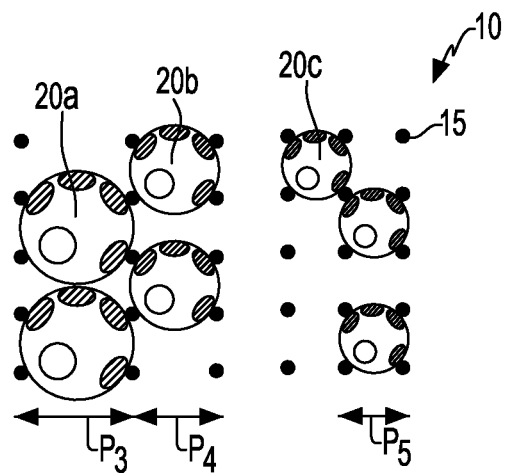
FIG. 3 is a top down planar view of an array of nanofibers for immobilizing matter, wherein the pitch separating adjacent nanofibers in the array is varied, in accordance with one embodiment of the present disclosure.

In one embodiment, a structure is provided for immobilizing cell matter that includes nano-structured, high-aspect-ratio nanofiber arrays, which may provide for temporal evaluation of cellular-level processes, such as cellulose biosynthesis (used as a specific example here). The term "array" as used to describe an array of nanofibers, i.e., nanofibers array, denotes a plurality of nanofibers. Nanofiber arrays 10 may be fabricated at defined pitch dimensions to provide three or four point pinning (also referred to as immobilization) of individual cell matter, such as protoplasts, as depicted in FIGS. 1A-3. As used throughout the present disclosure, the terms "pinning", "immobilizing" and/or "immobilization" means that cell matter 20 is being obstructed from movement so that the cell matter 20 is maintained in a fixed position. Immobilization may include elimination of both translation and rotation of the cell matter 20. FIGS. 1A and 1B depict immobilization of cell matter 20 by three point pinning. By "three point pinning" it is meant that the frictional force of the three nanofibers 15 that are in direct contact with the cell matter 20 physically immobilizes the cell matter 20. FIGS. 2A, 2B and 3 depict immobilization of cell matter 20 by four point pinning. By "four point pinning" it is meant that the frictional force of the four nanofibers 15 that are in direct contact with the cell matter 20 physically immobilizes the cell matter 20. In both three point and four point pinning the cell matter 20 may also be in direct contact with the substrate 5 that is present between the adjacent nanofibers 15 of the nanofiber array 10. During three point pinning an immobilized cell matter 20 is in contact with three nanofibers simultaneously, and during four point pinning an immobilized cell matter 20 is in contact with four nanofibers simultaneously. The term "simultaneously" as used to describe the contact of at least three adjacent nanofibers 15 in the array of nanofibers 10 when immobilizing cell matter 20 means that the at least three nanofibers 15 are in contact with the immobilized cell matter 20 at the same time.

The number of nanofibers 15 that are present in the nanofiber array 10 may be selected to correspond to the number of specimens of cell matter 20 that is intended to be immobilized in the nanofibers array 10, and whether immobilization is provided by three point pinning, as depicted in FIGS. 1A and 1B, and/or four point pinning, as depicted in FIGS. 2A, 2B and 3. In one embodiment, the number of nanofibers 15 that are present within the nanofibers array 10 may range from 10 nanofibers 15 to 100 nanofibers 15. In one example, the number of nanofibers 15 that are present in the nanofiber array 10 is equal to 25. The above examples for the number of nanofibers 15 that are present in the nanofibers array 10 is provided for illustrative purposes only, and is not intended to limit the present disclosure, as any number of nanofibers 15 may be present in the nanofibers array 10.

The term "nanofiber" denotes a structure having an aspect ratio that is greater than 25:1 (height: width) and has a tip with a width of 1 micron or less. The inter-nanofiber dimension (also referred to as interspike dimension) between each of the adjacent nanofibers 15 may be referred to as the "pitch" between adjacent nanofibers 15. Referring to FIGS. 1A-3, the pitch P1, P2, P3, P4, P5 is the center to center distance, i.e., nanofiber tip to adjacent nanofiber tip, between adjacent nanofibers 15. The pitch P1, P2, P3, P4, P5 in combination with the geometry and dimensions of each nanofiber 15 may be selected to correspond to the dimensions of the cell matter 20 that is intended to be immobilized. In some embodiments, the pitch P1, P2, P3, P4, P5 that is separating adjacent nanofibers 15 may be as great as 25 microns. In another embodiment, the pitch P1, P2, P3, P4, P5 may range from 10 microns to 20 microns. In one example, when the cell matter 20 being immobilized is protoplast, the pitch P1, P2, P3, P4, P5 is selected to immobilize cell matter 20 have a diameter ranging from 5 microns to 20 microns. In another example, when the cell matter 20 being immobilized is a yeast cell, the pitch P1, P2, P3, P4, P5 is selected to immobilize cell matter 20 have a diameter ranging from 2 microns to 5 microns.

The nanofiber 15 may be composed of carbon, and in some embodiments may be referred to as a "carbon nanofiber". The carbon nanofiber that provides the nanofibers 14 in the array of nanofibers may be a vertically aligned carbon nanofiber (VACNF). A vertically aligned carbon nanofiber is a carbon nanofiber in the height H1 of the carbon nanofiber is substantially perpendicular to the upper surface of the substrate 5 on which the nanofiber 15 is present. By substantially perpendicular it is meant that the angle defined at the intersection of the height H1 of the nanofiber 15 and the upper surface of the substrate 5 is +/−5° from normal.

Referring to FIGS. 1B and 2B, the aspect ratio of the nanofiber 15 is a ratio of the height H1 of the nanofiber 15 to the width W1 of the base of the nanofiber 15. In some embodiments, the nanofibers 15 that are employed to provide the array of nanofibers 10 in the methods and structures disclosed herein have an aspect ratio that is greater than 50:1, which in some examples may be greater than 100:1. The height H1 of the nanofiber 15 is measured from the tip of the nanofiber 15 to the base of the nanofiber 15 that is present in direct contact with the substrate 5 on which nanofiber 15 is present. In some embodiments, the height H1 of the nanofiber 15 may be as great as 100 microns. In one embodiment, the height H1 of the nanofiber 15 may range from 25 microns to 75 microns. In yet another embodiment, the height H1 of the nanofiber 15 may range from 35 microns to 65 microns. The width W1 of the base of the nanofiber 15 may be as great as 350 nm. In one embodiment, the width W1 of the base of the nanofiber 15 may range from 100 nm to 300 nm. In another embodiment, the width W1 of the base of the nanofiber 15 may range from 150 nm to 250 nm. The tip T1 of each nanofiber 15 may have a diameter that is as great as 150 nm. In another embodiment, the tip T1 of each nanofibers may range from 10 nm to 100 nm. It is noted that the aforementioned dimensions for the nanofibers 15 are provided for illustrative purposes only, and are not intended to limit the present disclosure to only the dimensions described above.

Referring to FIGS. 1A-3, in one embodiment, the array of nanofibers 15 is present on a substrate 5. The substrate 5 is typically transparent. The substrate 5 may be composed of a semiconductor material, such as a silicon-containing material, or a non-conductor, such as fused silica. Silicon-containing materials that are suitable for the substrate 5 include, but are not limited to, silicon (Si), single crystal silicon, polycrystalline silicon, amorphous silicon, and silicon-containing materials with some or all of the Si replaced by Ge. In one example, the silicon-containing material that provides the substrate 5 is silicon having a [100] crystal orientation. In another example, the substrate 5 is composed of fused silica. In one example, the substrate 5 is provided by a 4" wafer of [100] silicon. The thickness of the substrate 5 may range from 10 microns to 200 microns. In one example, the substrate 5 has a thickness of 170 microns.

In one embodiment, formation of the nanofiber array 10 may include the forming metal catalyst dots on a substrate 5 by with electron beam lithography (EBL) in conjunction with electron-gun metal evaporation, and catalytic growth of the nanofibers 10 on the substrate 5 using plasma enhanced chemical vapor deposition (PE-CVD). Growth of nanofibers 10, e.g., carbon nanofibers, may begin with the formation of a catalytic precursor. Nickel (Ni) can be used as a catalyst. However, other metals such as iron (Fe) and cobalt (Co) can also be utilized as the catalyst with these procedures.

The catalyst for nanofiber 10 growth, e.g., carbon nanofiber growth, may be formed on the substrate 5 by forming a metal catalyst dot. A catalyst dot is fabricated on the substrate 5 using photo or electron beam (e-beam) lithography and electron gun (e-gun) metal evaporation. More specifically, in one embodiment, the substrate 5 is first coated with a photoresist material, e.g., poly(methyl methacrylate) PMMA, and is then either photolithographically or e-beam exposed and developed to produce a small openings in the photoresist. Typically, each opening in the photoresist corresponds to the positioning of a later formed nanofiber 15 in the nanofiber array 10. Therefore, the pitch, i.e., center to center distance between adjacent openings in the photoresist, of the openings will correspond to the pitch of the nanofibers 15 in the nanofibers array 10.

Following the formation of the openings through the photoresist, a buffer layer is deposited within the openings in direct contact with the substrate 5 to prevent the formation of catalyst silicide and to impede catalyst diffusion at elevated temperatures. In one example, the buffer layer may be composed of titanium (Ti) or chrome (Cr). The buffer layer may have a thickness of 50 nm. The catalyst layer may then be deposited atop the buffer layer, wherein at least a portion of the catalyst layer is present in the openings. In one embodiment, the catalyst layer is composed of nickel (Ni), but the catalyst may also be composed of other metals suitable for growing nanofibers, e.g., carbon nanofibers, such as iron (Fe) and cobalt (Co). The catalyst layer may have a thickness of 50 nm.

In a following process step, isolated catalysts dots may be formed from the catalyst layer and the buffer layer on the substrate 5 by lifting the photoresist layer from the substrate 5. The photoresist layer may be lifted off the substrate in acetone, wherein the portion of the buffer layer and the catalyst layer that is present in the openings remains on the substrate to provide the metal catalyst dots for nanofibers growth. The portions of the catalyst layer and the buffer layer that are present on the portions of the photoresist layer between the openings is removed as the photoresist layers is lifted from the substrate 5. In one embodiment, the isolated catalyst dots may each have a diameter ranging from 350 nm to 650 nm. In another embodiment, the isolated catalyst dots have a diameter ranging from 400 nm to 600 nm. In one example, the isolated catalyst dots each have a diameter of 500 nm. By "isolated" it is meant that each catalyst dot is an island of material that is separate from an adjacent catalyst dot. The pitch separating adjacent catalyst dots may be as great as 100 microns. In one embodiment, the pitch separating adjacent catalyst dots may range from 3 microns to 20 microns. In another embodiment, the pitch separating adjacent catalyst dots may range from 5 microns to 10 microns.

In one embodiment, forming nanofibers 15, e.g., vertically aligned carbon nanofibers (VACNF), from the isolated catalyst dots includes the use of a direct current plasma enhanced chemical vapor deposition (DC-PECVD) that includes a vacuum chamber having an anode and a cathode present therein, in which the cathode may function as a heater. The details of one embodiment of DC plasma enhanced chemical vapor deposition a vacuum chamber including an anode and cathode for use in a plasma enhanced chemical vapor deposition have been described in U.S. Pat. No. 6,649,431, which is incorporated herein by reference. Although, the vertically aligned carbon nanofibers (VACNF) are described as being formed using DC-PECVD, embodiments have been contemplated in which radio-frequency (RF) or microwave plasmas also can be employed.

In some embodiments, for VACNF growth, a mixture of a carbonaceous gas and an etchant (e.g., acetylene and ammonia) can be used as the gas source. The etchant is needed to etch away graphitic carbon film that continuously forms during the growth from the plasma discharge. If not removed, the role of the film will be passivating the catalyst and thereby preventing the formation of VACNFs. Just prior to the VACNF growth process, ammonia can be introduced into the chamber and a plasma created. After the plasma is started, acetylene can be introduced and the VACNF growth can begin. Each catalyst dot, i.e., Ni (nickel) catalyst dot, initiates the formation of an individual VACNF. The catalyst dot can reside on top of the VACNF and provides for its continued catalytic growth upwards. In some embodiments, the VACNFs are oriented along plasma field lines and normally grow perpendicular to the substrate.

In some embodiments, the growth parameters may be adjusted to provide a nanofiber 15, e.g., VACNF, having an increasing diameter from the tip of the nanofiber to the base of the nanofiber 15. A nanofiber 15 having a base with a greater diameter than the tip of the nanofiber may be referred to as a carbon nanocone (CNC). One example of a growth parameter that may be adjusted to increase the diameter of the nanofiber 15 is the ratio of acetylene to ammonia. In this way, a CNC rather than a CNF can be formed. If the acetylene content is increased relative to that of ammonia (in addition to just diffusing through the Ni particle and precipitating at its bottom, thus providing for the growth in the vertical direction) carbon also begins to precipitate at the walls of the growing, initially cylindrical VACNF. Precipitation occurs due to the insufficient amount of the etchant (ammonia), which leads to the deposition rate of carbon being higher than the etching rate. Thus growth in two dimensions (vertical due to the catalytic growth through the catalyst dot, e.g., Ni particle, and lateral due to the carbon precipitation at the walls) occurs. The tip diameter of the CNC remains constant during the growth process and is determined only by the size of the catalyst dot. In contrast, at a given acetylene content the base diameter of the CNC increases with growth time. Furthermore, by changing growth parameters, such as the relative acetylene content, the angle of the sidewall (also referred to a cone angle) of the CNC can be changed. Higher acetylene content and higher pressure yield higher cone angles and vice versa. The CNC height is proportional to the growth time. The pitch of the carbon nanofibers, i.e., VACNF nanofibers or CNC nanofibers, is controlled by the patterning of the catalyst dots, as described above.

Referring to FIGS. 1A-3, in one specific example, formation of the nanofibers 15 in the array of nanofibers 10 may begin with forming a 50 nm thick nickel catalyst layer, on a 50 nm thick chrome buffer layer that is present on a 4" silicon [100] or transparent fused silica substrate 5. The catalyst layer and the buffer layer may then be photolithographically patterned or e-beam patterned to provide catalyst dots with a 500 nm diameter at a desired pitch (i.e. 5, 10, or 20 microns) over the entire surface, or select regions, of the substrate 5. Nanofibers 15, i.e., carbon nanofibers, may then be synthesized in a DC-PECVD reactor at a temperature of 650° C., 10 torr, 2 A, using a mixture of a carbonaceous source gas (acetylene) and an etch gas (ammonia). Growth time is selected to provide nanofibers 15 of desired length, typically ranging from approximately 10 microns to 17 microns tall, with tip diameters of approximately 100 nm.

Referring to FIGS. 1A, 2A and 3, the pitch P1, P2, P3, P4, P5 separating the adjacent nanofibers 15 in the array of nanofibers 10 is typically equal to the pitch separating the adjacent catalyst dots. The pitch P1, P2 separating adjacent nanofibers 15 in the array of nanofibers 10 may be uniform (also referred to as homogenous) as depicted in FIGS. 1A and 2A, or the pitch P3, P4, P5 may be graded (also referred to as varied) to correspond to cell matter 20 of different diameters, as depicted in FIG. 3. The pitch P1, P2, P3, P4, P5 on nanofiber arrays can be homogenous across the entire substrate 5, or may be spatially varied in discrete increments or continuously varied across the substrate 5.

These defined nanofiber pitches may be used to immobilize cell matter 20, such as protoplasts, in various geometric configurations. Referring to FIGS. 1A and 2B, homogenous pitches P1, P2 will tend to immobilize cell matter 20, such as protoplasts, of a specific diameter, based upon the pitch and wedging of the protoplasts between nanofibers. Referring to FIG. 3, variable nanofiber pitch P3, P4, P5 across a nanofiber array 10 can be used to immobilize cell matter 20, such as protoplasts, of varying diameters. Referring to FIGS. 1A-3, the placement of nanofibers 15 may also be used to hold cell matter 20 in close proximity to one another, or with discrete intervals between individual or groups of cell matter 20. In one example, such spatial variation of protoplast immobilization can be important when communication or diffusion of growth factors and other species between protoplasts may influence the digestion or synthesis of cellulose of individual protoplasts. In some embodiments, the pitch P1, P2, P3, P4, P5 may be as great as 100 microns. In one embodiment, the pitch P1, P2, P3, P4, P5 separating adjacent nanofibers 15 in the array of nanofibers 10 may range from 3 microns to 20 microns. In another embodiment, the pitch P1, P2, P3, P4, P5 separating adjacent nanofibers 15 in the array of nanofibers 10 may range from 5 microns to 10 microns.

Referring to FIGS. 4-8B, the array of nanofibers 10a, 10b, 10c, 10d, 10e, 10f, 10g may be positioned within a fluidic channel 25 or is in communication with a series of fluidic channels 25. In some embodiments, the fluidic channel 25 may be employed for delivering the cell matter 20 to the array of nanofibers 10a, 10b, 10c, 10d, 10e, 10f, 10g, or for delivering reagents R1, R2, R3 to the cell matter 20 that is immobilized on the array of nanofibers 10a, 10b, 10c, 10d, 10e, 10f. In one embodiment, the fluidic channel 25 is provided by walls 26 that formed on the substrate 5 using photolithography. For example, the walls 26 that define the fluidic channel 25 may be formed by depositing a photoresist layer on the substrate 5, patterning the photoresist layer, and then developing the photoresist layer. Photoresists are classified into two groups: positive resists and negative resists. A positive resist is a type of photoresist in which the portion of the photoresist that is exposed to light becomes soluble to the photoresist developer. The portion of the photoresist that is unexposed remains insoluble to the photoresist developer. A negative resist is a type of photoresist in which the portion of the photoresist that is exposed to light becomes insoluble to the photoresist developer. The unexposed portion of the photoresist is dissolved by the photoresist developer.

In some embodiments, the photoresist may be composed of the Poly(vinyl cinnamate), Poly(methyl methacrylate) (PMMA), Poly(methyl glutarimide) (PMGI), Phenol formaldehyde resin (DNQ/Novolac) or multi-layers and combinations thereof. In one example, the photoresist that provides the walls 26 of the micro-channel is provided by an epoxy-based negative photoresist that is commonly referred to as SU-8. SU-8 is explained in more detail in U.S. Pat. No. 4,882,245, which is incorporated herein by reference. One derivative of SU-8 that is suitable for use with the methods and structures of the present disclosure is SU8: 2020.

In one embodiment, to form the walls 26 of the fluidic channel 25, a layer of photoresist layer may be deposited on the upper surface of the substrate 5 using spin on deposition, spray coating or chemical solution deposition. The layer of photoresist may have a thickness ranging from 20 microns to 200 microns. In one example, the layer of photoresist that provides the walls 26 of the micro-fluidic channel 25 may have a thickness of 60 microns. The layer of photoresist may be patterned and developed to form walls 26 that define the fluidic channel 25. By "patterned" it is meant that the layer of photoresist is selectively irradiated to light through a stencil, e.g., reticle, that is designed to allow light to fall only on preselected areas of the layer of the photoresist, e.g., areas that define a plurality of walls 26 that provide the fluidic channel 25. The light causes a chemical change, e.g., cross-linking, in the layer of photoresist. The stencil (hereafter referred to as a reticle) may include a transparent substrate and a pattern layer. The radiant energy blocking portion may be comprised of chrome, chrome oxide, chromium nitride, iron oxide, silicon or a number of other opaque materials.

The radiation, i.e., light, that may be used to expose the layer of photoresist through the reticle may include UV, DUV, and the H and I lines of a mercury-vapor lamp. In another embodiment, the layer of photoresist may be exposed with an ion beam. Depending upon whether the photoresist is a positive resist or a negative resist, either the exposed portion or the unexposed portion of the layer of photoresist may be washed away, i.e., removed, using a developer. Examples of developers for use with positive resists include sodium hydroxide (NaOH) and tetramethyl ammonium hydroxide (TMAH) to be used in combination with a water rinse ($H_2O$). Examples of developers for use with negative resists include xylene with a rinse composed of n-Butylacetate. In one embodiment, the developer for SU-8 is 1-Methoxy-2-propanol acetate.

In one embodiment, the walls 26 of the fluidic channel 25 may be provided by a dielectric material, such as an oxide, nitride or oxynitride, that is patterned and etched using photolithography. In this embodiment, the material layer that provides the dielectric material may first be deposited on the substrate, a mask of photoresist may be formed on the dielectric material, and the exposed portions of the dielectric material may be etched while the portions of the dielectric material are under and protected by the photoresist mask. The exposed portions of the dielectric material may be removed by an etch process that is selective to the photoresist mask and the substrate. The remaining portions of the dielectric material following selective etching provides the walls 26 of the fluidic channel 25.

Referring to FIGS. 4-8B, in some embodiments, the walls 26 of the fluidic channel 25 may provide a chamber for housing the array of nanofibers 10a, 10b, 10c, 10d, 10e, 10f, 10g, and a plurality of inlets for introducing a suspension of cell matter 20 to be caged on the array of nanofibers 10a, 10b, 10c, 10d, 10e, 10f for optical viewing. The inlets 27 of the micro-fluidic channel 25 may also be employed to introduce reagents and buffer solutions to the array of nanofibers 10a, 10b, 10c, 10d, 10e, 10f that are housed by the chamber of the fluidic channel 25.

The walls 26 of the fluidic channel 25 may be formed after forming the array of nanofibers 10. In one example, following the formation of the array of nanofibers 10a, 10b, 10c, 10d, 10e, 10f, 10g, the micro-fluidic channel 25 is fabricated upon a 170 micron thick fused silica substrate, in which the walls 26 of the micro-fluidic channel 25 are composed of SU-8 crosslinkable epoxy photoresist that has been photolithographically patterned with UV light. In one embodiment, prior to depositing the photoresist material that provides the walls 26, the array of nanofibers 10a, 10b, 10c, 10d, 10e, 10f, 10g are first protected beneath a thin, uniform protective layer of photoresist, such as SU8 epoxy. In one example, to deposit the protective layer of photoresist, the substrate 5 including the array of nanofibers 10a, 10b, 10c, 10d, 10e, 10f, 10g may be spun with a photoresist of a 1:3 dilution of SU8 2002:SU8 thinner. The deposited protective photoresist may then be cured. In one embodiment, the deposited protective photoresist may be cured with a first prebaked at 60° C. for 1 minute followed by a second prebake at 90° C. for 2 minutes. The protective photoresist may then be exposed to 10 seconds of UV light. The wafer is then treated with a post baked that may include a first heat treatment for 1 minute at 60° C. followed by a second heat treatment for 2 minutes at 90° C. In some embodiments, the protective layer of photoresist anchors the base of the nanofibers 15 in the array of nanofibers 10a, 10b, 10c, 10d, 10e, 10f, 10g to the substrate 5. In some examples, this anchorage step protects the nanofibers 15 from shearing off from the substrate 5 during handling.

Following the formation of the protective layer of photoresist, the fluidic channels 25 may then be defined on the substrate 5 including the array of nanofibers 10a, 10b, 10c, 10d, 10e, 10f, 10g. In one example, the walls 26 of the micro-fluidic channel 25 may be formed by depositing layers of photoresist, such as SU8 epoxy. The layers of photoresist that provide the walls 26 of the micro-fluidic channel 25 may then be cured using a pre-exposure bake including a first treatment at 60° C. for 1 minute followed by a second treatment at 90° C. for 3 minutes. The layers of photoresist that provide the walls 26 of the fluidic channel 25 may then be lithography patterned with a desired channel layout. The substrate 5 is then post exposure baked at 60° C. for 1 minute and 90° C. for 4 minutes. The substrate 5 including the array of nanofibers 10a, 10b, 10c, 10d, 10e, 10f, 10g and the patterned photoresist layers for the walls 26 of the fluidic chamber 25 are then developed in SU8 developer for 2 minutes and rinsed in isopropyl alcohol. The above process sequence, in which the array of nanofibers 10a, 10b, 10c, 10d, 10e, 10f, 10g is formed before the walls 26 of the fluidic channel 25 is provided for illustrative purposes only, and is not intended to limit the present disclosure. For example, embodiments have been contemplated, in which the walls 26 of the fluidic channel 25 are formed before the array of nanofibers 10a, 10b, 10c, 10d, 10e, 10f, 10g.

Immobilization of cell matter 20 within the array of nanofibers 10, 10a, 10b, 10c, 10d, 10e, 10f, 10g depicted in FIGS. 1-8B can be achieved using various techniques. In one embodiment, cell matter 20 may be immobilized onto the array of nanofibers 10, 10a, 10b, 10c, 10d, 10e, 10f, 10g using a centrifuge. A centrifuge is a piece of equipment, generally driven by a motor, that puts an object in rotation around a fixed axis, applying a force perpendicular to the axis. The centrifuge works using sedimentation principles, where the centripetal acceleration causes more dense substances to separate out along the radial direction, i.e., toward the bottom of the centrifuge tube. By the same principle, lighter objects will tend to move to the top, i.e., to the top of the centrifuge tube (in the rotating picture, move to the center). In one embodiment, the nanofiber array may be positioned flat at the bottom of a centrifuge tube facing upwards, and a fluid containing cell matter 20 is positioned within the centrifuge tube, wherein as the centrifuge tube is run through the centrifuge, the cell matter 20, e.g., protoplasts, are forced from the fluid containing the cell matter onto the array of nanofibers 10, 10a, 10b, 10c, 10d, 10e, 10f, 10g. The cell matter 20 is immobilized when in contact with three nanofibers in the embodiments in which the array of nanofibers 10 provides three point pinning, as depicted in FIGS. 1A-1B, and is immobilized when in contact with four nanofibers in the embodiments in which the array of nanofibers 10, 10a, 10b, 10c, 10d, 10e, 10f, 10g provide four point pinning, as depicted in FIGS. 2A-8B.

The fluid containing cell matter may be a suspension of cell matter 20. A suspension is a heterogeneous fluid containing solid particles that are sufficiently large for sedimentation. For example, solids particles suitable for sedimentation may be larger than 1 micrometer. The suspension of cell matter 20 may include any dispersion medium. For example, when the cell matter 20 is protoplasts the dispersion medium may consist of an aqueous solution containing an osmoticum (example mannitol or magnesium sulfate) and a protectant (calcium chloride). The solution may also include other additives to avoid flocculation of the cell matter, such as dispersants.

Various commercially available tubes are available for swinging bucket centrifuges that facilitate orienting a substrate upon a platform so that may then be placed into a centrifuge, which orients the centripetal force normal to the flat substrate surface during the centrifugation procedure. For fixed angle rotors (not swinging bucket), substrates 5 including nanofiber arrays 10, such as those described above with reference to FIGS. 1A-3 may be fixed within centrifuge tubes first filling the centrifuge tube with a small amount of uncrosslinked polydimethylsiloxane (PDMS) (silicone rubber) and curing the PDMS while spinning the centrifuge, thereby creating a slanted substrate 5 that the nanofiber arrays 10 may be positioned upon, normal to the centripetal force. It is noted that the present disclosure is not limited to only uncrosslinked PDMS, as other materials may be converted from a liquid to a solid material within the centrifuge tube during spinning, to provide a surface normal to the centripetal force.

Referring to FIGS. 1A-8B, in another embodiment, immobilization of the cell matter 20 onto the array of nanofibers 10, 10a, 10b, 10c, 10d, 10e, 10f, 10g may be achieved by pipetting a suspension of the cell matter 20 directly down onto the array of nanofibers 10, 10a, 10b, 10c, 10d, 10e, 10f, 10g. In this embodiment, the suspension of the cell matter 20 may be allowed to settle upon the array of nanofibers 10, 10a, 10b, 10c, 10d, 10e, 10f, 10g without additional centripetal force. More secure immobilization of the settled cell matter 20 from the suspension can be achieved by pipetting a liquid against the settled cell matter 20 to further press the cell matter 20 into the array of nanofibers 10, 10a, 10b, 10c, 10d, 10e, 10f, 10g. The density of the solution used should not exceed the density of the cell matter being delivered in order to avoid buoyant forces which would interfere with immobilization of the material within the Nanofiber matrices.

An advantage of using immobilized cell matter 20 upon the arrays of nanofibers 10, 10a, 10b, 10c, 10d, 10e, 10f, 10g depicted in FIGS. 1-8B is that they may be integrated with fluidic channels 25 to facilitate reagent delivery, exchange, active transport studies, and diffusional transport studies of the immobilized cell matter 20, e.g., protoplasts. Micro-fluidic reagent delivery can be used to perfuse the sample, i.e., immobilized cell matter 20, with various nutrients, growth factors, digestive enzymes, or other relevant species. In some embodiments, the use of transparent substrates 5, such as fused silica substrates, enables the use of laser scanning microscopy on the immobilized cell matter 20. In the embodiments, in which the immobilized cell matter 20 is a protoplast, laser scanning microscopy may provide for high resolution imaging of cellulose degradation or biosynthesis. The fluidic channels 25 may be configured to provide a closed system or an open system.

Figure 4:
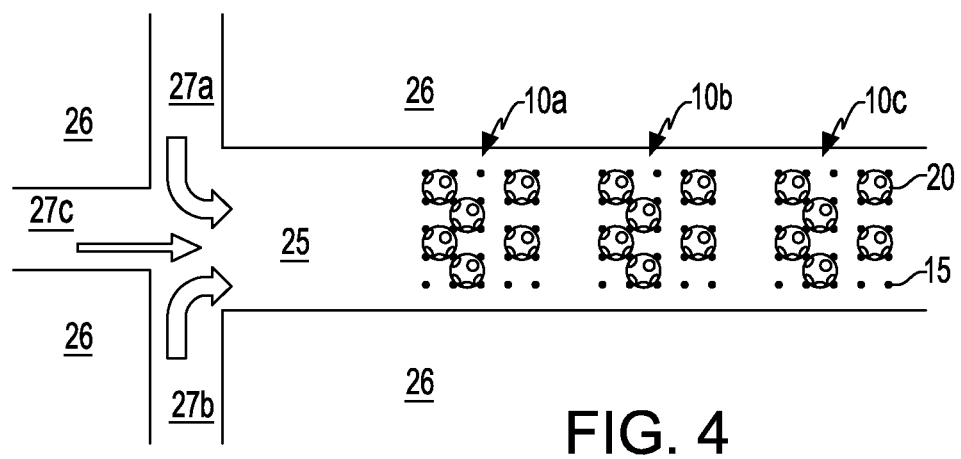
FIG. 4 is a top down planar view of a structure for immobilizing matter that includes a channel for delivery of a fluid containing matter, and an array of nanofibers that is present in the channel for immobilizing the matter, in accordance with one embodiment of the present disclosure.

Referring to FIG. 4, fluidic channels 25 having arrays of nanotubes 10a, 10b, 10c present therein may be loaded with cell matter 20, such as protoplasts, using a variety of methods including centrifugation in a swinging bucket centrifuge, as described above with reference to FIGS. 1A-3, or by allowing settling of a protoplasts suspension, or by pipetting a protoplast suspension down onto the array of nanofibers 10a, 10b, 10c present within the chamber of the fluidic channel 25. Once the cell matter 20 has been immobilized on the array of nanofibers 10a, 10b, 10c the fluidic channel 25 may be sealed. For example, the fluidic channel 25 may be sealed by aspirating excess buffer solution from the portions of the fluidic channel 25 that dose not include the chamber in which the array of nanofibers 10a, 10b, 10c is present, and placing a cover onto the device. In one example, the cover that seals the fluidic channel 25 may be composed of silicone, e.g., polydimethylsiloxane (PDMS). In some embodiments, the cover that seals the fluidic channel 25 may feature at least one opening therethrough to provide for fluidic access ports to the chamber of the fluidic channel 25 in which immobilized cell matter 20 is present on the array of nanofibers 10a, 10b, 10c.

In one embodiment, the fluidic channels 25 may be used to control the delivery of nutrients and/or growth factors to the immobilized cell matter 20, e.g., immobilized protoplasts, that are present on the array of nanofiber 10a, 10b, 10c that are present in the chamber of the micro-fluidic channel 25, and to control the flow of metabolic by-products between immobilized cell matter 20. In one embodiment, in which the cell matter 20 is provided by protoplasts, based upon the microfluidic layout and cell matter immobilization locations, protoplasts may be located downstream of one another at downstream arrays of nanofibers 10b, 10c such that downstream protoplasts can experience the metabolic byproducts of upstream cell matter 20 that is immobilized on upstream arrays of nanofibers 10a.

Figure 5:
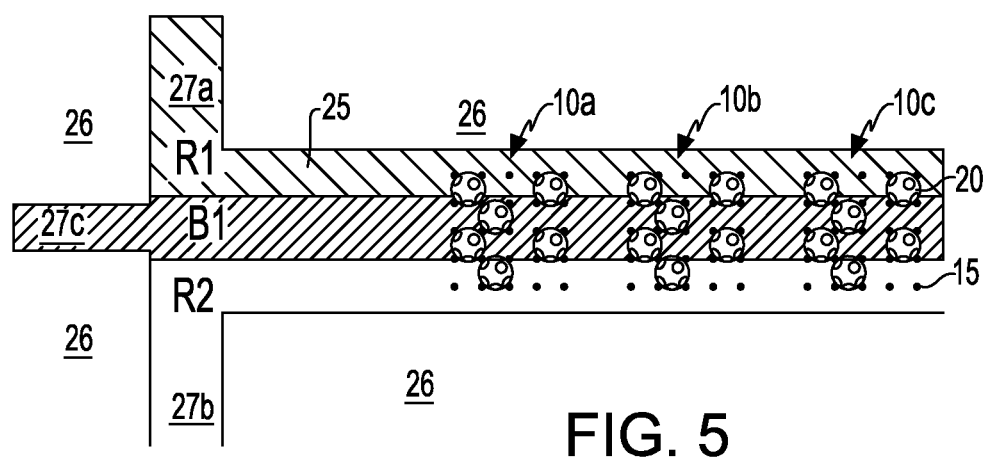
FIG. 5 is a top down planar view of applying two reagents microfluidically to the matter immobilized on the array of nanofibers depicted in FIG. 4, wherein the reagents are separated from one another by a buffer, in accordance with one embodiment of the present disclosure.

In another embodiment, arrays of nanofibers may also be located so that the cell matter 20, such as protoplasts, do not experience one another's metabolic byproducts, either by locating them in isolated fluidic channels (not depicted). In yet another embodiment, the laminar flow characteristics of the fluidic channels 25 may be employed to minimize movement of reagents and metabolic byproducts within the chamber of the fluidic chamber 25 in which the arrays of nanofibers 10a, 10b, 10c are present, as depicted in FIG. 5. For example, referring to FIG. 5, the first and second inlets 27a, 27b that are present at opposing sides of the chamber containing the arrays of nanofibers 10a, 10b, 10c may be employed to apply reagents R1, R2 to the cell matter 20 that is immobilized on the arrays of nanofibers 10a, 10b, 10c, and a buffer solution B1 may be introduced to a chamber by the inlet 27c that is between the first and second inlets 27a, 27b, wherein the buffer solution B1 separates the first and second reagents R1 as they flow down the fluidic chamber 25.

In the embodiment depicted in FIG. 5, the cell matter 20, e.g., protoplasts, that are immobilized on the side of the chamber of the fluidic channel 25 that is closest to the first inlet 27a is only subjected to the first reagent R1 that is introduced to the chamber through the first inlet 27a, and the cell matter 20, e.g., protoplasts, that are immobilized on the side of the chamber of the fluidic channel 25 that is closest to the second inlet 27b is only subjected to the second reagent R2 that is introduced to the chamber through the second inlet 27b. The buffer solution B1 that is introduced to the chamber by the third inlet 27b separates the first reagent R1 from the second reagent R2, wherein the cell matter 20 that is immobilized on the arrays of nanofibers 10a, 10b, 10c in the center of the chamber are only subjected to the buffer solution B1, and not the first and second reagents R1, R2. Examples of the first and second reagents R1, R2 that may be applied to the cell matter 20 include at least one reagent selected from the group consisting of nutrients, growth factors, digestive enzymes and combinations thereof. For example, the first reagent may be a cell wall digesting/degrading enzyme, cellulase; the second reagent may be pectinase, separated by a buffer solution without a digestive component. The first reagent may be cellulase and the second reagent may be a combination of cellulase and hemicellulase; thereby enabling the observation of how the addition of hemicellulase impacts cell wall digestion on one side of the plant cell vs. not having hemicellulase in the microfluidic flow on the other side of the same cell. The buffer solution B1 may include at least one fluid that is selected from the group consisting of water, and water with osmoticums and stabilizers to preserve the integrity of a fully protoplasted plant cell, including mannitol, sorbital, magnesium sulfate, calcium chloride, and combinations thereof.

Figure 6:
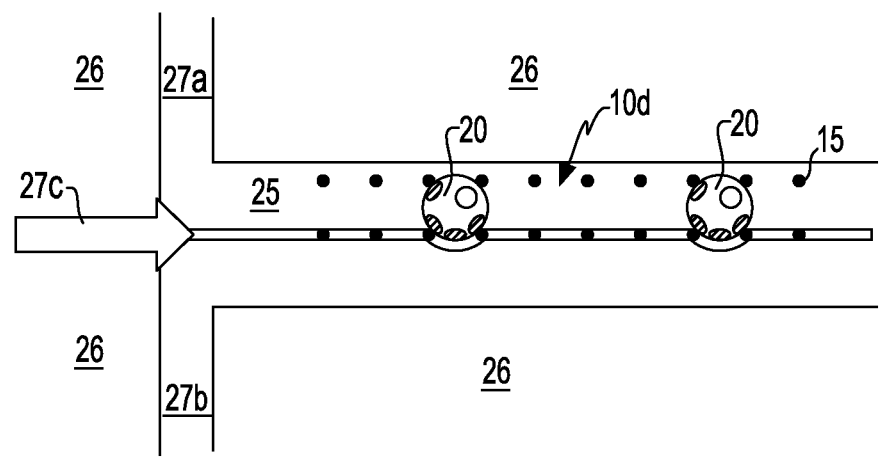
FIG. 6 is a top down planar view of applying a reagent to a specific portion of immobilized matter in an array of nanofibers, in accordance with one embodiment of the present disclosure.

In another embodiment of the present disclosure, techniques may be used to control reagent delivery with spatial resolution at or below the diameter of an individually selected cell matter 20, such as protoplasts, that are immobilized on an array of nanofibers 10d, as depicted in FIG. 6. For example, by using pinched injection techniques, one may expose immobilized protoplasts to highly spatially resolved reagent delivery. In one example in which the cell matter 20 is provided by protoplasts, a reagent such as 3-IAA (indole acetic acid) or a molecular agent can be delivered to just one side of an appropriately positioned protoplast or set of protoplasts to observe the impact of this reagent on those protoplasts in comparison to the protoplasts immediately adjacent thereto that are not exposed to the reagent due to the fluid delivery arrangement.

In one example, in which the immobilized cell matter 20 is protoplasts, the micro-fluidic mixing techniques described above with reference to FIGS. 1-8B may be used to evaluate the impact of serial dilutions of growth factors, or reagents on cellulose regeneration, or the dilution of digestive enzymes on cellulose degradation of the protoplasts. The fluid paths to the immobilized cell matter 20, e.g., protoplasts, may be configured to provide serial dilution either using electrokinetic or hydrodynamic pumping techniques. The cell matter 20 that is immobilized in the fluid paths may be treated with specific dilutions of species and can be evaluated either in real-time, or at discrete time intervals using optical microscopy. For example, immobilized protoplasts may be exposed to a steady stream of indole-3-acetic acid as various dilutions in protoplast buffer solution for a 24 hr period, followed by brief exposure to fluorescein diacetate and calcofluor to observe cell viability and cellulose synthesis. Following dye delivery, the dye may be washed from the system using neat protoplast buffer. Following imaging, the protoplasts can once again be perfused with 3-IAA in protoplast buffer for an extended period.

Figure 7:
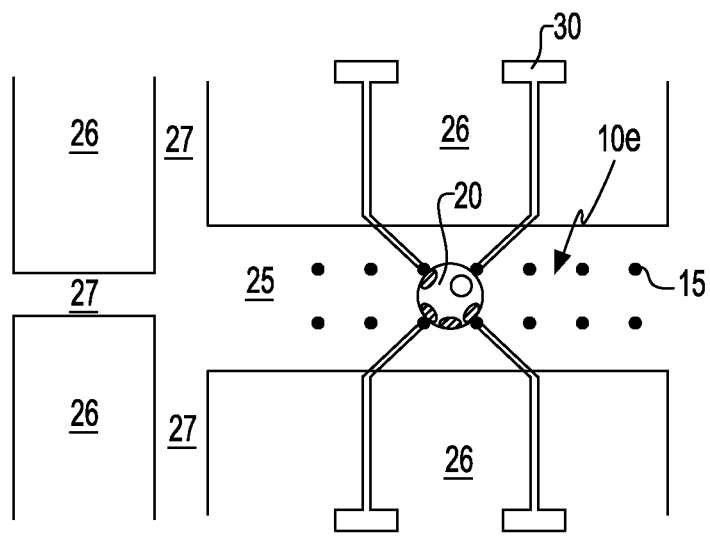
FIG. 7 is a top down planar view of a structure for immobilizing matter including an array of nanofibers in which the individual nanofibers may be electrically addressed for use as electrochemical sensors, in accordance with one embodiment of the present disclosure.
Figure 8A:
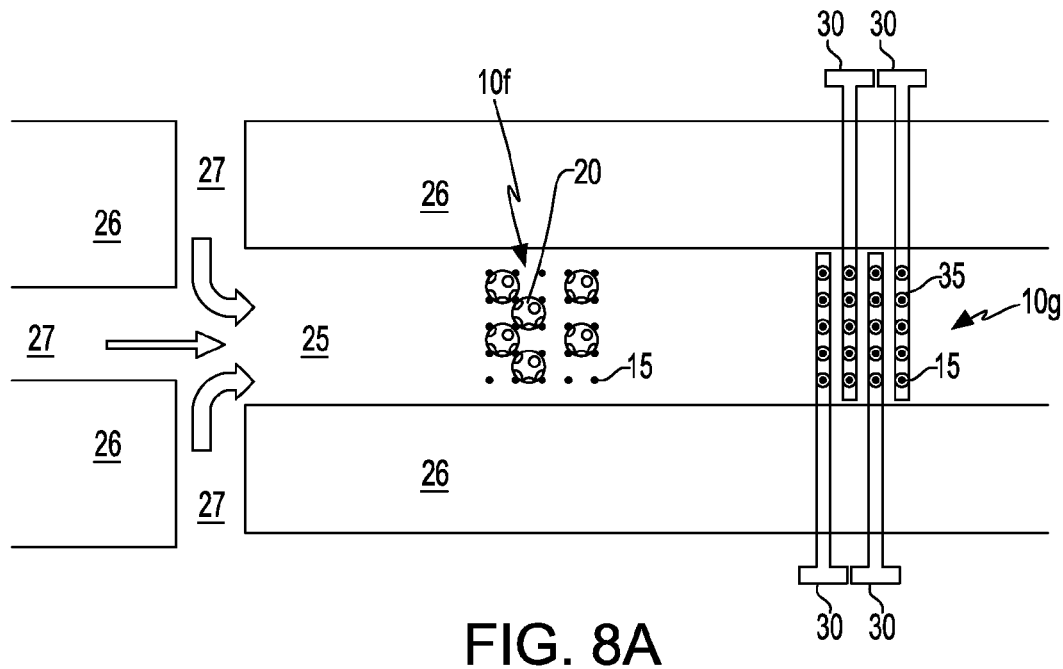
FIG. 8A is a top down planar view of a structure is provided for immobilizing matter, and measuring emissions by the immobilized matter in response to stimuli applied to the immobilized matter, in accordance with one embodiment of the present disclosure.
Figure 8B:
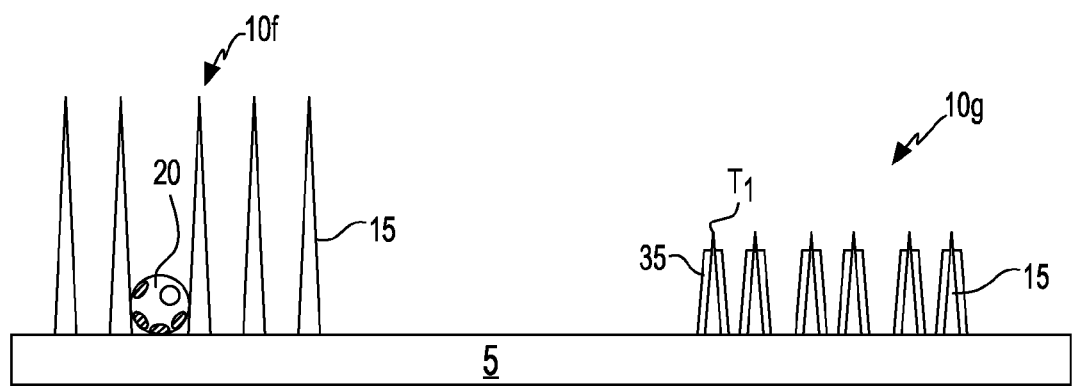
FIG. 8B is a side cross sectional view of the structure depicted in FIG. 8A along section line B-B.

Referring to FIGS. 7-8B, in addition to immobilization scaffolding, the arrays of nanofibers 10e, 10g may provide active electrochemical probing elements to locally and temporally monitor specific analytes with high spatial resolution. In one embodiment, individual or groups of nanofibers 15 may be configured with electrical contacts (hereafter referred to as interconnect) such that the nanofiber 15 may be used as an electrode. In one embodiment, nanofibers within the arrays of nanofibers 10e, 10g may provide an electrode by forming an electrically conductive interconnect 30 on at least a part of the substrate 5, and growing at least one nanofiber 15, e.g., carbon nanofiber, that is coupled to the electrically conductive interconnect 30. As used herein, the term "electrically conductive" means a material having a room temperature conductivity of greater than $10^{-8}$ $(\Omega\text{-m})^{-1}$. The electrically conductive interconnect 30 can be made from any metal or combination of metals that survive the deposition process for forming the nanofibers 15, such as the temperature of the DC-PECVD process used to provide VACNF. For example, the electrically conductive interconnect 30 may include one, or more, refractory metal(s), such as, for example, tungsten (W), molybdenum (Mo), tantalum (Ta), niobium (Nb), platinum (Pt), aluminum (Al) and combinations thereof. The electrically conductive interconnect 30 may be formed using deposition processes, such as physical vapor deposition (PVD), e.g., sputtering. Following deposition, the metal layer may be patterned and etched to provide the geometry that is desired for the electrically conductive interconnect 30. One example of an etch process for etching the metal that provides the electrically conductive interconnect 30 is reactive ion etch.

In some embodiments, an insulating layer (not shown) may be formed on the substrate 5 prior to the formation of the interconnect structure 30, in which the insulating layer may be patterned and provides for electrical isolation between adjacent interconnects 30. Following the formation of the interconnects 30 on the substrate 5, the nanofibers, e.g., vertically aligned carbon nanofibers (VACNF), may be formed on the interconnects 30 using the methods described above. To summarize, to form the nanofibers 15, a buffer layer is formed in direct contact with the with the electrically conductive interconnects 30, followed by the formation of a catalyst layer, wherein the stack of the buffer layer and the catalyst layer is patterned to provide catalyst dots. In the embodiments in which the nanofibers function as electrodes, the catalyst dots are in direct contact with the electrically conductive interconnects 30. Following formation of the catalyst dots, the nanofibers 15, e.g., carbon nanofibers, may be formed using a chemical vapor deposition process, such as direct current plasma enhanced chemical vapor deposition (DC-PECVD), using a mixture of a carbonaceous gas and an etchant, e.g., acetylene and ammonia. The details for forming the nanofibers 15 have been described above with reference to FIGS. 1-3. Carbon nanofibers are suitable for use as electrodes, because of their electrical conductivity, but other materials have been contemplated for the nanofibers 15 that provide the electrodes, and are within the scope of the present disclosure.

In some embodiments, the active probe site of the electrode is provided by only the tip T1 of the nanofiber 15. To provide that only the tip T1 of the nanofiber 15 is the active probe site for the electrodes, the sidewalls of the nanofibers 15 may be passivated with a dielectric material. For example, a dielectric sheath 35 may be present on the sidewalls of the nanofibers 15 in the array of nanofibers 10e, 10g that provide the electrodes. The tip T1 of the nanofiber 15 that is not covered by the dielectric sheath 35 and provides the active probe side of the electrode may have a diameter ranging from 3 nm to 150 nm. In another embodiment, the tip of the nanofiber 15 may have a diameter ranging from 10 nm to 100 nm. The length of the tip of the nanofiber 15 that provides the active probe site may be as great as 200 microns. In one embodiment, the tip of the nanofiber 15 that provides the active probe site may range from 50 microns to 100 microns.

In some embodiments, the dielectric sheath 35 may be provided by silicon oxide ($SiO_2$), silicon nitride, and/or an insulating polymer. The dielectric sheath 35 may be deposited on the nanofibers 15 of the arrays of nanofibers 10e, 10g using a conformal deposition process, such as spin on deposition or chemical vapor deposition (CVD). The thickness of the dielectric sheath 35 may range from 25 nm to 100 nm. In another embodiment, the thickness of the dielectric sheath 35 may range from 50 nm to 75 nm. In some embodiments, the dielectric sheath 35 may be removed from the tip of the nanofibers 15 using an etch process. Typically, the etch process for removing the material of the dielectric sheath 35 from the tip T1 of the nanofibers 15 is an anisotropic etch. For example, the tip of the nanofibers may be exposed by removing the dielectric sheath 35 with reactive ion etch (RIE). The etch process for removing the material of the dielectric sheath 35 is typically selective to the nanofiber 15, e.g., carbon nanofiber. In one embodiment, the etch chemistry for removing the portion of the dielectric sheath 35 from the tip of the nanofibers 15 comprises $CF_4:O_2$ and/or $CF_4:SF_6$. Further details for depositing the material layer that provides the dielectric sheath 35, and the etch process for removing the material layer that provides the dielectric sheath from the tip T1 of the nanofibers 15 are described in greater detail in U.S. Pat. No. 6,9892,519, which is incorporated herein by reference.

Typically, the tip T1 of the nanofiber 15 that provides the active probe site of the electrodes provided by the array of nanofibers 10e, 10g is separated from the base and sidewalls 26 of the channel 25. By positioning the active probe site of the electrodes centrally within the channel 25, the electrodes provided by the arrays of nanofibers 10e, 10g disclosed herein reduce measurement errors that results from interactions between the subject matter being measured and the sidewalls 26 and the base of the channel 25. More specifically, it has been determined that interactions between the cell matter 20 and emissions by the immobilized cell matter 20 when interacting with the sidewalls 26 and the base of the channel 25 result in band broadening of the signals being electrochemically measured. By moving the active probe site of the electrodes to only the tip T1 of the nanofibers 15 in the arrays of nanofibers 10e, 10g, the active probe site of the electrodes is moved away from the structures of the channel 25 that interfere with the cell matter 20 and the emissions by the immobilized cell matter 20 that is being electrochemically measured. More specifically, in some embodiments, by moving the active probe site of the electrodes to only the tip T1 of the nanofibers 15, the electrodes provided by the nanofiber arrays 10e, 10b substantially eliminates resolution degradation that occurs from smearing of the cell matter 20 and smearing of emissions by the cell matter against the sidewalls 26 and base of the channel 25, substantially eliminating band-broadening effects.

FIGS. 8A and 8B depict one embodiment of a structure for analyzing cell matter response to external stimuli. In some embodiment, the structure for analyzing cell matter includes a fluidic channel 25 for delivery of a fluid containing cell matter, and an array of nanofibers 10f, 10g that is present within the fluidic channel 25. The fluidic channel 25 that is depicted in FIGS. 8A and 8B is similar to the fluidic channel 25 that has been described above with reference to FIGS. 1-7. Therefore, the description of the fluidic channel 25 depicted in FIGS. 1-7 is suitable for the fluidic channel 25 that is depicted in FIGS. 8A and 8B.

The array of nanofibers 10f, 10g includes a first portion of nanofibers 10f that is present at an opening of the fluidic channel 25 and a second portion of nanofibers 10g that is present at the exit of the fluidic channel 25. The first portion of nanofibers 10f has a pitch to physically engage cell matter 20 from the fluid containing cell matter being traversed through the fluidic channel 25 from the opening to the exit. The first portion of nanofibers 10f for immobilizing the cell matter 20 is similar to the array of nanofibers 10, 10a, 10b, 10c, 10d that have been described above with reference to FIGS. 1-6. Therefore, the description of the array of nanofibers 10, 10a, 10b, 10c, 10d depicted in FIGS. 1-6 is suitable for the first portion nanofibers 10f that are depicted in FIGS. 8A and 8B. In one example, the adjacent nanofibers 15 in the first portion nanofibers 10f have a pitch that ranges from 5 microns to 20 microns. In one example, the tip diameter of each nanofiber 15 in the first portion nanofibers 10f ranges from 10 nm to 100 nm, and the base of each nanofiber 15 in the first portion of nanofibers 10f is as great as 350 nm.

The second portion nanofibers 10g within the fluidic channel 25 is downstream of the first portion of nanofibers 10f and provides electrodes having active probe sites that are physically separated from sidewalls 26 and base of the fluidic channel 25. The electrodes provided by the second portion nanofibers 10g may be employed for analyzing emissions by the cell matter 20 that is immobilized on the first portion of nanofibers 10f. In some embodiments, block masks composed of photoresist may be employed to allow for separate processing of the regions of the substrate 5 in which the first portion of the nanofibers 10f and the second portion of the nanofibers 10g are present.

In some embodiments, the structures depicted in FIGS. 8A and 8B may be employed to optically and electrochemically analyze cell matter 20 simultaneously. For example, fluid containing cell matter may be traversed through the fluidic channel 25 across the first portion of nanofibers 10f before being traversed across the second portion of nanofibers 10g. As the fluid containing cell matter is traversed past the first portion of nanofibers 10f, at least a portion of the cell matter 10 contained within the fluid containing cell mater is immobilized by the first portion of nanofibers 10f. The immobilized cell matter 10 that is present on the first portion of nanofibers 10f may be imaged using laser scanning microscopy, scanning electron microscope (SEM), atomic force microscope or a combination thereof.

Once the cell matter 20 is immobilized on the first portion of nanofibers 10f, a stimuli may be applied to the cell matter 20. Stimuli may be applied to the cell matter 20 by dispersing the stimuli in a liquid medium and flowing the stimuli through the channel 25 across the immobilized cell matter 20. The stimuli may include nutrients, growth factors, digestive enzymes, or other relevant species. In one example, when the cell matter is a plant cell, the stimuli may be an enzyme that degrades the cell wall of the plant cell, including but not limited to cellulase, hemicellulase, pectinase. The stimuli may be hormones that modulate cellulosic synthesis of the cell wall, including auxins and synthetic auxins such at naphthalene-1 acetic acid. The stimuli can include antibodies, which bind to the surface of the cell, and interact with the cell. The stimuli can include fluorescently labeled species, which interact or bind with specific receptors on the cell surface.

In some embodiments, the cell matter 20 that is engaged to the first portion nanofibers 10f may be imaged while applying of the stimuli to the immobilized cell matter 20.

Emissions by the immobilized cell matter 20 in response to the stimuli may be measured electrochemically by the second portion of nanofibers 10g that is present in the fluidic channel 25 downstream from the first portion of nanofibers 10f. Some examples of emissions by the immobilized cell matter 20 that can be measured by the electrodes provided by the second portion of nanofibers 10g include electroactive species such as some auxins, easily oxidized or reduced degradation products of the cell wall, electroactive peptides, and electroactive signaling species, and alditols and carbohydrates derives from cell wall digestion. Some examples of electrical measurements that can be taken by the electrodes provided by the second portion of nanofibers 10g includes fast scan cyclic voltammetry, amperometry, cyclic voltammetry, differential pulse voltammetry and combinations thereof. In one example, when the cell matter 20 is a plant cell and the stimuli applied to the immobilized plant cell degrades the cell wall of the plant cell, the emissions being measured by the electrodes of the second portion of nanofibers 10g can be the fragments of the plant cell's degraded cell wall, which can be measured by amperometry by clamping the electrode nanofiber at sufficiently high potential to oxidize the components digesting from the cell well (i.e. carbohydrate and glycoproteins).

While the present disclosure has been particularly shown and described with respect to preferred embodiments thereof, it will be understood by those skilled in the art that the foregoing and other changes in forms and details may be made without departing from the spirit and scope of the present disclosure. It is therefore intended that the present disclosure not be limited to the exact forms and details described and illustrated, but fall within the scope of the appended claims.

What is claimed is:

1. A method of analyzing protoplasts comprising:
 providing a channel and an array of nanofibers within the channel, wherein a first portion of the array comprises carbon nanofibers and has a pitch between adjacent carbon nanofibers that immobilizes protoplasts; and a second portion of the array of nanofibers is separated from walls of the channel and provides at least one electrode;
 passing a fluid that is a suspension of protoplasts in a liquid medium, through the channel, wherein the fluid is traversed across the first portion of the array of carbon nanofibers before the second portion of the array of nanofibers, wherein as the fluid is traversed past the first portion of the array of carbon nanofibers, at least some of the protoplasts are immobilized by the first portion of the array of carbon nanofibers, wherein each immobilized protoplast wedges between and simultaneously contacts at least three carbon nanofibers of the first portion of the array;
 applying a stimuli to the immobilized protoplasts; and
 measuring emissions by the immobilized protoplasts in response to the stimuli with the at least one electrode that is provided by the second portion of the array of nanofibers.

2. The method of claim 1 further comprising imaging the immobilized protoplasts while the stimuli is applied to the immobilized protoplasts.

3. The method of claim 2, wherein said imaging comprises laser scanning microscopy, scanning electron microscope (SEM), or atomic force microscopy.

4. The method of claim 1, wherein measuring the emissions by the immobilized protoplasts in response to the stimuli is performed with a plurality of electrodes that is provided by the second portion of the array of nanofibers.

5. The method of claim 1, wherein the passing of the fluid through the channel comprises pipetting the fluid onto the first portion of the array of carbon nanofibers.

6. The method of claim 1, wherein the second portion of the array of nanofibers is an array of carbon nanofibers, and wherein at least one carbon nanofiber in the second portion of the array of carbon nanofibers includes a base in direct contact with an interconnect, a dielectric sheath present on a carbon nanofiber sidewall, and an exposed nanofiber tip, wherein the exposed nanofiber tip provides an active probe site of the at least one electrode.

7. The method of claim 1, wherein the stimuli is adding a material selected from the group consisting of nutrients, growth factors, digestive enzymes, antibodies against cell surface receptors, other ligands to cell surface receptors, and solutions containing components that can influence the immobilized protoplasts.

8. The method of claim 1, wherein the measuring of the emissions comprises an electroanalytical technique to detect materials exuded from the immobilized protoplasts, said exuded materials selected from the group consisting of carbohydrates, glucoproteins and electroactive species.

9. The method of claim 7, wherein the solution that contains components that can influence the immobilized protoplasts contains microbes or viruses.

10. The method of claim 8, wherein the electroanalytic technique to detect material exuded from the immobilized protoplasts is selected from the group consisting of:
 amperometry, cyclic voltammetry, potentiometric measurements and potentiostatic measurements.

* * * * *